United States Patent
O'hAimhirgin

(10) Patent No.: US 10,058,524 B2
(45) Date of Patent: Aug. 28, 2018

(54) METHODS FOR IMPROVING JOINT FUNCTION

(71) Applicant: Tersus Life Sciences, LLC, Bonita Springs, FL (US)

(72) Inventor: Lochlainn O'hAimhirgin, Mentor, OH (US)

(73) Assignee: TERSUS LIFE SCIENCES, LLC, Bonita Springs, FL (US)

( * ) Notice: Subject to any disclaimer, the term of this patent is extended or adjusted under 35 U.S.C. 154(b) by 122 days.

(21) Appl. No.: 15/047,222

(22) Filed: Feb. 18, 2016

(65) Prior Publication Data

US 2016/0235702 A1    Aug. 18, 2016

Related U.S. Application Data

(60) Provisional application No. 62/117,561, filed on Feb. 18, 2015.

(51) Int. Cl.
| | | |
|---|---|---|
| *A61K 31/201* | (2006.01) | |
| *A61K 31/20* | (2006.01) | |
| *A61K 45/06* | (2006.01) | |
| *A61K 31/165* | (2006.01) | |
| *A61K 31/167* | (2006.01) | |
| *A61K 31/192* | (2006.01) | |
| *A61K 31/728* | (2006.01) | |

(52) U.S. Cl.
CPC .......... *A61K 31/201* (2013.01); *A61K 31/165* (2013.01); *A61K 31/167* (2013.01); *A61K 31/192* (2013.01); *A61K 31/20* (2013.01); *A61K 31/728* (2013.01); *A61K 45/06* (2013.01)

(58) Field of Classification Search
CPC ...... A61K 31/201; A61K 31/20; A61K 45/06; A61K 31/165; A61K 31/167; A61K 31/192; A61K 2300/00
USPC ............................ 514/77, 169, 182; 424/402
See application file for complete search history.

(56) References Cited

U.S. PATENT DOCUMENTS

| | | | |
|---|---|---|---|
| 2005/0208162 A1* | 9/2005 | Spencer ................. | A61K 31/20 424/769 |
| 2006/0183797 A1* | 8/2006 | Cohen .................... | A61K 31/20 514/546 |
| 2008/0311167 A1* | 12/2008 | Oronsky .............. | A61K 9/0014 424/402 |
| 2011/0039928 A1 | 2/2011 | Golini | |
| 2011/0065627 A1 | 3/2011 | Barathur et al. | |
| 2012/0225941 A1 | 9/2012 | Green | |

OTHER PUBLICATIONS

International Search Report and Written Opinion for PCT Appl. Ser. No. PCT/US2016/018479 dated May 3, 2016.
Fraser et al., "Changes in plasma free fatty acid concentrations in rheumatoid arthritis patients during fasting and their effects upon T-lymphocyte proliferation", Rheumatology, 1999, vol. 38: pp. 948-952.
International Preliminary Report on Patentability for PCT Appl. Ser. No. PCT/US2016/018479 dated Aug. 31, 2017 (6 pages).

\* cited by examiner

*Primary Examiner* — Yih-Horng Shiao
(74) *Attorney, Agent, or Firm* — Foley & Lardner LLP; James F. Ewing

(57) ABSTRACT

The present technology provides methods for improving joint function in a subject in need thereof. The methods include administering to the subject an effective amount of a composition comprising one or more of C16:1n7-palmitoleate, derivatives thereof, or pharmaceutically acceptable salts thereof.

17 Claims, 11 Drawing Sheets

FIG. 2

| | Palmitoleic Acid | Placebo | | p-Value Δ |
|---|---|---|---|---|
| | Mean ±SD (n) Within Group P Value δ | Mean ±SD (n) Within Group P Value δ | | |
| Time of Onset of Minimum Discomfort or Pain Level (min) | | | | |
| Day 0 Baseline | 0.57 ± 0.43 (20) | 0.67 ± 0.50 (20) | | -- |
| Day 7 | 1.01 ± 0.83 (20) | 0.93 ± 0.89 (20) | | - |
| Day 30 End of Study | 1.51 ± 1.42 (20) | 1.42 ± 0.71 (20) | | - |
| Change from Day 0 to Day 7 | 0.44 ± 0.72 (20) p = 0.013* | 0.26 ± 0.88 (20) p = 0.195* | PA 40% > PL | 0.736* |
| Change from Day 0 to Day 30 | 0.94 ± 1.32 (20) p = 0.005* | 0.75 ± 0.74 (20) p < 0.001* | PA 20% > PL | 0.428* |
| Time of Onset of Maximum Discomfort or Pain Level (min) | | | | |
| Day 0 Baseline | 5.53 ± 2.32 (20) | 5.94 ± 2.40 (20) | | -- |
| Day 7 | 6.48 ± 1.86 (20) | 5.89 ± 2.91 (20) | | - |
| Day 30 End of Study | 6.89 ± 2.59 (20) | 5.43 ± 2.53 (20) | | - |
| Change from Day 0 to Day 7 | 0.95 ± 2.54 (20) p = 0.111* | -0.05 ± 2.54 (20) p = 0.931* | | 0.279* |
| Change from Day 0 to Day 30 | 1.37 ± 2.21 (20) p = 0.012* | -0.51 ± 1.83 (20) p = 0.232* | PA 64% > PL | 0.007* | n, number; SD, standard deviation; Min, minimum; Max, maximum
Δ Between group comparisons were made using ANCOVA
δ Within-group comparisons were made using the paired Student t-test.
* Logarithmic transformation required to achieve normality.
Probability values P≤0.05 are statistically significant.

FIG. 3

| | Palmitoleic Acid | Placebo | | p-Value $^\Delta$ |
| --- | --- | --- | --- | --- |
| | Mean ±SD (n) Within Group P Value $^\delta$ | Mean ±SD (n) Within Group P Value $^\delta$ | | |
| Time of Offset of Minimum Discomfort or Pain Level (min) | | | | |
| Day 0 Baseline | 0.49 ± 0.70 (20) | 0.38 ± 0.25 (20) | | - |
| Day 7 | 0.54 ± 0.87 (20) | 0.40 ± 0.45 (20) | | - |
| Day 30 End of Study | 0.29 ± 0.21 (20) | 0.60 ± 0.76 (20) | | - |
| Change from Day 0 to Day 7 | 0.05 ± 1.21 (20) p = 0.844* | 0.02 ± 0.51 (20) p = 0.846* | | 0.969* |
| Change from Day 0 to Day 30 | -0.20 ± 0.74 (20) p = 0.239* | 0.22 ± 0.77 (20) p = 0.218* | | 0.201* |
| Time of Offset of Maximum Discomfort or Pain Level (min) | | | | |
| Day 0 Baseline | 2.27 ± 1.36 (20) | 2.46 ± 1.57 (20) | | - |
| Day 7 | 1.98 ± 1.38 (20) | 1.97 ± 1.43 (20) | | - |
| Day 30 End of Study | 1.33 ± 0.95 (20) | 1.80 ± 1.35 (20) | | - |
| Change from Day 0 to Day 7 | -0.29 ± 1.91 (20) p = 0.506* | -0.49 ± 1.53 (20) p = 0.168* | | 0.824* |
| Change from Day 0 to Day 30 | -0.94 ± 1.55 (20) p = 0.014* | -0.66 ± 1.46 (20) p = 0.056* | PA 30% > PL | 0.412* | n, number; SD, standard deviation; Min, minimum; Max, maximum
$\Delta$ Between group comparisons were made using ANCOVA
$\delta$ Within-group comparisons were made using the paired Student t-test.
* Logarithmic transformation required to achieve normality.
Probability values P≤0.05 are statistically significant.

FIG. 4

|  | Palmitoleic Acid | Placebo |  | P-Value Δ |
|---|---|---|---|---|
|  | Mean ±SD (n) Within Group P Value δ | Mean ±SD (n) Within Group P Value δ |  |  |
| Distance Walked (m) | | | | |
| Day 0 Baseline | 473 ± 98 (20) | 504 ± 63 (20) |  | - |
| Day 7 | 488 ± 89 (20) | 497 ± 113 (20) |  | - |
| Day 30 End of Study | 511 ± 85 (20) | 518 ± 83 (20) |  | - |
| Change from Day 0 to Day 7 | 14 ± 61 (20) p = 0.300 | -7 ± 87 (20) p = 0.733 | PA 150% > PL | 0.494 |
| Change from Day 0 to Day 30 | 38 ± 75 (20) p = 0.036 | 14 ± 46 (20) p = 0.187 | PA 63% > PL | 0.415 | n, number; SD, standard deviation; Min, minimum; Max, maximum
Δ Between group comparisons were made using ANCOVA
δ Within-group comparisons were made using the paired Student t-test.
Probability values P≤0.05 are statistically significant.

FIG. 5

| | Palmitoleic Acid | Placebo | | P-Value [Δ] |
|---|---|---|---|---|
| | Mean ±SD (n) Within Group P Value [δ] | Mean ±SD (n) Within Group P Value [δ] | | |
| | Left Knee Extension (Degrees) | | | |
| Day 0 Baseline | 71.8 ± 11.2 (20) | 80.8 ± 9.3 (20) | | - |
| Day 7 | 74.8 ± 9.8 (20) | 75.8 ± 10.8 (20) | | - |
| Day 30 End of Study | 78.1 ± 11.9 (20) | 79.8 ± 9.1 (20) | | - |
| Change from Day 0 to Day 7 | 3.0 ± 10.4 (20) p = 0.203 | -5.0 ± 9.8 (20) p = 0.035 | PA 266% > PL or 3X better | 0.236 |
| Change from Day 0 to Day 30 | 6.3 ± 11.8 (20) p = 0.028 | -1.0 ± 7.0 (20) p = 0.530 | PA 131% > PL or 7X better | 0.256 |
| | Right Knee Extension (Degrees) | | | |
| Day 0 Baseline | 74.8 ± 9.9 (20) | 77.6 ± 10.0 (20) | | - |
| Day 7 | 75.8 ± 10.6 (20) | 76.7 ± 11.6 (20) | | - |
| Day 30 End of Study | 75.2 ± 13.2 (20) | 78.3 ± 9.8 (20) | | - |
| Change from Day 0 to Day 7 | 1.0 ± 9.2 (20) p = 0.616 | -0.9 ± 9.2 (20) p = 0.668 | PA 190% > PL or 2X better | 0.701 |
| Change from Day 0 to Day 30 | 0.4 ± 11.9 (20) p = 0.867 | 0.8 ± 7.7 (20) p = 0.668 | PA 100% < PL | 0.696 | n, number; SD, standard deviation; Min, minimum; Max, maximum
Δ Between group comparisons were made using ANCOVA
δ Within-group comparisons were made using the paired Student t-test.
Probability values P≤0.05 are statistically significant.

FIG. 6

|  | Palmitoleic Acid | Placebo |  | p-Value Δ |
|---|---|---|---|---|
|  | Mean ±SD (n) Within Group P Value δ | Mean ±SD (n) Within Group P Value δ |  |  |
| Left Knee Flexion (Degrees) | | | | |
| Day 0 Baseline | 111.2 ± 19.5 (20) | 123.3 ± 14.9 (20) | - | |
| Day 7 | 116.5 ± 16.6 (20) | 119.2 ± 15.5 (20) | - | |
| Day 30 End of Study | 123.7 ± 16.7 (20) | 124.0 ± 15.4 (20) | - | |
| Change from Day 0 to Day 7 | 5.2 ± 13.1 (20) p = 0.093 | -4.1 ± 11.7 (20) p = 0.135 | PA 178% > PL | 0.166 |
| Change from Day 0 to Day 30 | 12.4 ± 20.8 (20) p = 0.015 | 0.8 ± 11.5 (20) p = 0.774 | PA 94% > PL | 0.279 |
| Right Knee Flexion (Degrees) | | | | |
| Day 0 Baseline | 117.3 ± 12.5 (20) | 117.8 ± 16.6 (20) | - | |
| Day 7 | 117.8 ± 19.5 (20) | 117.0 ± 14.8 (20) | - | |
| Day 30 End of Study | 125.0 ± 13.8 (20) | 121.5 ± 12.8 (20) | - | |
| Change from Day 0 to Day 7 | 0.4 ± 13.0 (20) p = 0.878 | -0.8 ± 11.9 (20) p = 0.766 |  | 0.768 |
| Change from Day 0 to Day 30 | 7.8 ± 13.5 (20) p = 0.019 | 3.6 ± 13.3 (20) p = 0.235 | PA 54% > PL | 0.292 | n, number; SD, standard deviation; Min, minimum; Max, maximum
Δ Between group comparisons were made using ANCOVA
δ Within-group comparisons were made using the paired Student t-test.
Probability values P≤0.05 are statistically significant.

FIG. 7

| | Palmitoleic Acid | Placebo | | P-Value † |
|---|---|---|---|---|
| | Mean ±SD (n) Within Group P Value ‡ | Mean ±SD (n) Within Group P Value ‡ | | |
| Time Spent Doing Aerobic Exercise (min/week) | | | | |
| Day 0 Baseline | 174 ± 109 (20) | 148 ± 146 (20) | | 0.179 |
| Day 7 | 174 ± 125 (20) | 172 ± 136 (20) | | - |
| Day 30 End of Study | 205 ± 159 (20) | 166 ± 118 (20) | | - |
| Change from Day 0 to Day 7 | 0 ± 67 (20) p = 0.844 | 23 ± 97 (20) p = 0.351 | 23 X better for placebo | 0.302 |
| Change from Day 0 to Day 30 | 31 ± 107 (20) p = 0.450 | 18 ± 80 (20) p = 0.221 | PA 42% > PL or 1.7 X better for PA | 0.848 |
| Time Spent Doing Stretching Exercise (min/week) | | | | |
| Day 0 Baseline | 43 ± 62 (20) | 45 ± 47 (20) | | 0.538 |
| Day 7 | 43 ± 58 (20) | 58 ± 66 (20) | | - |
| Day 30 End of Study | 68 ± 67 (20) | 50 ± 53 (20) | | - |
| Change from Day 0 to Day 7 | 0 ± 53 (20) p = 0.918 | 13 ± 55 (20) p = 0.442 | 13 X better for placebo | 0.850 |
| Change from Day 0 to Day 30 | 26 ± 57 (20) p = 0.066 | 5 ± 47 (20) p = 0.572 | PA 81% > PL or 5 X better for PA | 0.608 | n, number; SD, standard deviation; Min, minimum; Max, maximum
† Between group comparisons were made using the Mann-Whitney U test.
‡ Within group comparisons were made using the Signed-Rank test.
Probability values P≤0.05 are statistically significant.

FIG. 8

| PROPRIETARY PURIFIED PALMITOLEIC ACID: PHYSICAL COMPONENT SUMMARY SCORE¹ | | n | Mean | Std. Deviation | Std. Error Mean | Sig. | Percent Change (Other timepoint versus Baseline) |
|---|---|---|---|---|---|---|---|
| Pair 1 | Baseline (Visit 2) | 19 | 46.93 | 6.810 | 1.562 | 1.000 | 3.36% |
| | Day 7 (Visit 3) | 19 | 48.51 | 5.263 | 1.207 | | |
| Pair 2 | Baseline (Visit 2) | 19 | 46.93 | 6.810 | 1.562 | 0.031* | 8.93% |
| | Day 30 (Visit 4) | 19 | 51.12 | 3.867 | 0.887 | | |
| PLACEBO: PHYSICAL COMPONENT SUMMARY SCORE² | | n | Mean | Std. Deviation | Std. Error Mean | Sig. | Percent Change (Other timepoint versus Baseline) |
| Pair 1 | Baseline (Visit 2) | 20 | 44.81 | 6.606 | 1.477 | 0.020* | 7.23% |
| | Day 7 (Visit 3) | 20 | 48.05 | 6.530 | 1.460 | | |
| Pair 2 | Baseline (Visit 2) | 19 | 45.09 | 6.672 | 1.531 | 0.008** | 15.53% |
| | Day 30 (Visit 4) | 19 | 52.09 | 6.836 | 1.568 | | |

Note¹: Significant testing was performed using Sign Test.
Note²: Significant testing was performed using Paired Sample t-Test for Pair 1 and Sign Test for Pair 2.
**Significant at alpha=0.01
*Significant at alpha=0.05

FIG. 9

|  | Palmitoleic Acid | Placebo |  | P-Value [Δ] |
| --- | --- | --- | --- | --- |
|  | Mean ±SD (n)<br>Within Group P Value [δ] | Mean ±SD (n)<br>Within Group P Value [δ] |  |  |
| Knee Related Quality of Life Subscale Score | | | | |
| Day 0<br>Baseline | 45.6 ± 17.7 (20) | 52.8 ± 13.2 (20) |  | - |
| Day 7 | 54.1 ± 19.4 (20) | 55.0 ± 15.4 (20) |  | - |
| Day 30<br>End of Study | 60.6 ± 17.2 (20) | 66.2 ± 16.8 (20) |  | - |
| Change from<br>Day 0 to<br>Day 7 | 8.4 ± 10.4 (20)<br>p = 0.002 | 2.2 ± 12.4 (20)<br>p = 0.439 | PA 74% > PL or 3.8 X better for PA | 0.164 |
| Change from<br>Day 0 to<br>Day 30 | 15.0 ± 15.2 (20)<br>p < 0.001 | 13.4 ± 17.7 (20)<br>p = 0.003 | PA 11% > PL | 0.715 | n, number; SD, standard deviation; Min, minimum; Max, maximum
Δ Between group comparisons were made using ANCOVA
δ Within-group comparisons were made using the paired Student t-test.
Probability values P≤0.05 are statistically significant.

METHODS FOR IMPROVING JOINT FUNCTION

CROSS-REFERENCE TO RELATED APPLICATIONS

This application claims the benefit of and priority to U.S. Application No. 62/117,561, filed Feb. 18, 2015, the contents of which are incorporated herein by reference in their entireties.

TECHNICAL FIELD

The present technology relates generally to methods for improving joint function in a subject in need thereof comprising administering to the subject an effective amount of a composition comprising C16:1n7-palmitoleate, or derivatives or pharmaceutically acceptable salts thereof.

BACKGROUND

The following description is provided to assist the understanding of the reader. None of the information provided or references cited is admitted to be prior art.

About 52.5 million (22.7%) adults in the United States suffer from physician-diagnosed arthritis. About 43% of those with arthritis report arthritis-attributable activity limitation (AAAL), making arthritis the most common cause of disability among adults aged 65 years or older. Arthritis is widespread among patients with multiple chronic conditions including heart disease, diabetes, and obesity, with prevalence rates of 49%, 47%, and 31%, respectively. Arthritis causes patients to become less physically active, thus impacting their quality of life. About 44% of adults with arthritis report no time for physical activity mostly due to concerns that physical activity would aggravate their pain. As people age, their joints become stiffer and less flexible, which can subsequently result in joint pain. Several non-arthritic factors causing knee discomfort include unusual exertion or overuse of joints, strains or sprains, fractures, bursitis, viral infections, chondromalacia patella, and synovial impingement.

In addition to surgery, other known methods of treating joint pain include prescription drugs (e.g., OxyContin®, Percocet®, Vicodin®, Bextra®, Celebrex® etc.), over-the-counter medicines (such as aspirin, Advil®, Aleve®, Motrin® etc.), and complementary/alternative medicine (e.g., acupuncture). Unfortunately, all of these methods are plagued with harmful contraindications, or, when sufficient data is available, have been shown to provide temporary relief at best. Accordingly, there is a need for effective methods of treatment that address joint pain and provide a safe, less invasive alternative to surgery. Additionally, there is a need for treatment methods that are easy to use, and can be performed by pain sufferers without the assistance of others.

SUMMARY OF THE PRESENT TECHNOLOGY

In one aspect, the present technology provides a method for improving joint function in a subject in need thereof comprising administering to the subject an effective amount of a composition comprising one or more of C16:1n7-palmitoleate, a C16:1n7-palmitoleate derivative, or a pharmaceutically acceptable salt thereof.

In some embodiments of the method, the composition also includes C16:0-palmitate, a C16:0-palmitate derivative, or a combination thereof.

Additionally or alternatively, in some embodiments of the method, the composition also includes C18:1n9-oleate, a C18:1n9-oleate derivative, or a combination thereof.

In some embodiments of the method, the subject experiences joint pain while engaging in moderate, hard, or very hard physical activity. In certain embodiments, the subject is human. In some embodiments of the method, the affected joint is the knee, shoulder, elbow, forearm, wrist, hip, ankle, or foot.

Additionally or alternatively, in some embodiments, the method includes simultaneously, sequentially, or separately administering at least one additional therapeutic agent.

Additionally or alternatively, in some embodiments of the method, the composition is administered orally, topically, systemically, intravenously, subcutaneously, intraperitoneally, or intramuscularly.

In some embodiments of the method, the composition is administered daily for 1, 2, 3, 4 weeks or more.

In some embodiments, administration of the composition causes an increase in the time of onset of maximum discomfort or pain level in the subject. In some embodiments, the time of onset of maximum discomfort or pain level in the subject is increased by at least 20%. In some embodiments, the time of onset of maximum discomfort or pain level in the subject is increased by at least 30%. In some embodiments, the time of onset of maximum discomfort or pain level in the subject is increased by at least 50%. In some embodiments, the time of onset of maximum discomfort or pain level in the subject is increased by at least 75%.

In some embodiments, the time of onset of maximum discomfort or pain level in the subject is increased within one week following the administration of the composition to the subject. In some embodiments, the time of onset of maximum discomfort or pain level in the subject is increased by at least 20% within one week following the administration of the composition to the subject.

In some embodiments, the time of onset of maximum discomfort or pain level in the subject is increased within one month following the administration of the composition to the subject. In some embodiments, the time of onset of maximum discomfort or pain level in the subject is increased by at least 30% within one month following the administration of the composition to the subject.

In some embodiments, administration of the composition causes an increase in the range of joint motion in the subject. In some embodiments, the range of joint motion is increased by at least 10%.

In some embodiments of the method, the range of joint motion is increased within one month following the administration of the composition to the subject. In some embodiments of the method, the range of joint motion is increased within three weeks following the administration of the composition to the subject. In some embodiments of the method, the range of joint motion is increased within two weeks following the administration of the composition to the subject. In some embodiments of the method, the range of joint motion is increased within one week following the administration of the composition to the subject.

In some embodiments, the range of joint motion is increased by at least 10% within one month following the administration of the composition to the subject.

BRIEF DESCRIPTION OF THE DRAWINGS

FIG. 2 shows the comparison of (a) the time of onset of minimum discomfort or pain level and (b) the time of onset of maximum discomfort or pain level between the C16:1n7-palmitoleate-treated and placebo groups.

FIG. 3 shows the comparison of (a) the time of offset of minimum discomfort or pain level and (b) the time of offset of maximum discomfort or pain level between the C16:1n7-palmitoleate-treated and placebo groups.

FIG. 4 shows the comparison of the average distance walked in six minutes at Day 0, Day 7, and Day 30 between the C16:1n7-palmitoleate-treated and placebo groups.

FIG. 5 shows the comparison of left knee and right knee extension measurements between the C16:1n7-palmitoleate-treated and placebo groups.

FIG. 6 shows the comparison of left knee and right knee flexion measurements between the C16:1n7-palmitoleate-treated and placebo groups.

FIG. 7 shows the comparison of the average time per week spent doing aerobic exercises and stretching exercises between the C16:1n7-palmitoleate-treated and placebo groups.

FIG. 8 shows the comparison of the physical component score of the SF-12 survey between the C16:1n7-palmitoleate-treated and placebo groups.

FIG. 9 shows the comparison of the knee-related quality of life scores survey between the C16:1n7-palmitoleate-treated and placebo groups.

DETAILED DESCRIPTION

Figure 1:
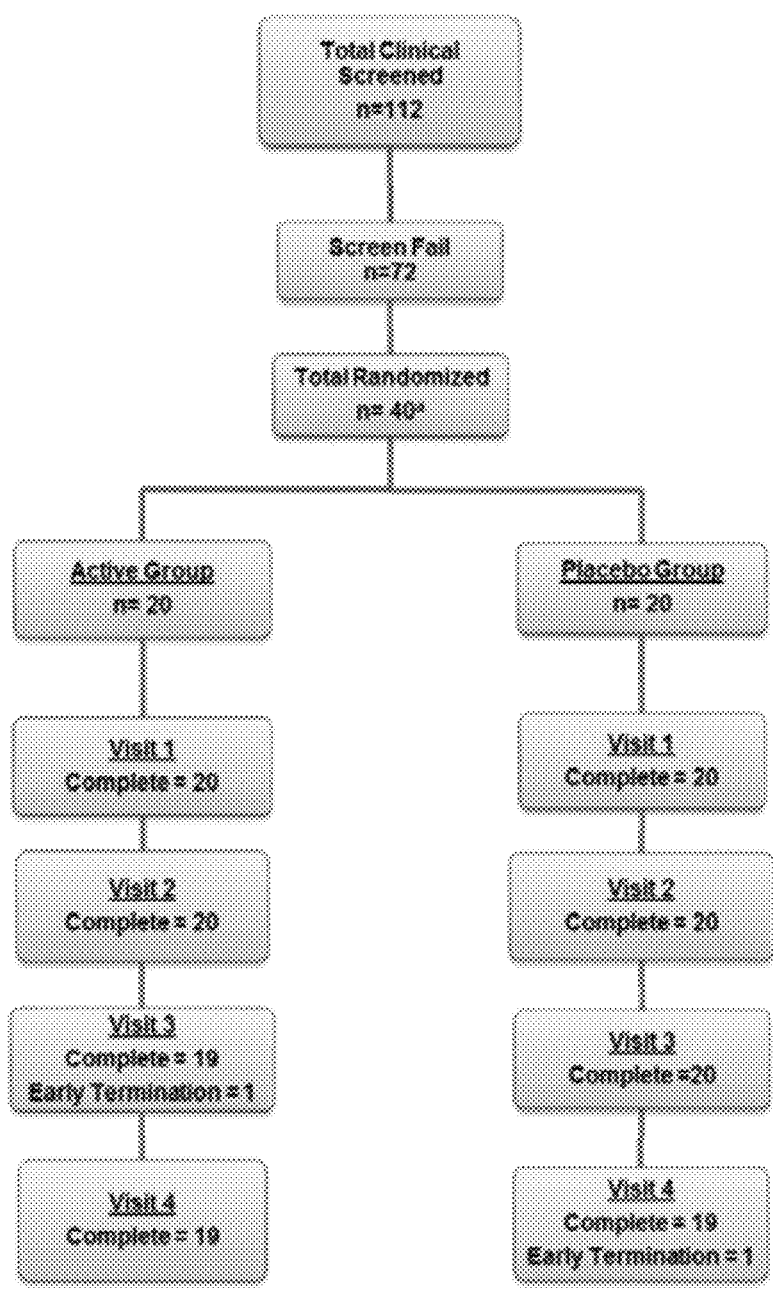
FIG. 1 shows the overall study design for evaluating the effect of C16:1n7-palmitoleate administration on joint function.

It is to be appreciated that certain aspects, modes, embodiments, variations and features of the present technology are described below in various levels of detail in order to provide a substantial understanding of the present technology.

The definitions of certain terms as used in this specification are provided below. Unless defined otherwise, all technical and scientific terms used herein generally have the same meaning as commonly understood by one of ordinary skill in the art to which this present technology belongs.

As used in this specification and the appended claims, the singular forms "a", "an" and "the" include plural referents unless the content clearly dictates otherwise. For example, reference to "a compound" includes a plurality of compounds.

As used herein, the terms "approximately" or "about" in reference to a number are generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the term "composition" includes therapeutic and dietary formulations including, but not limited to a dietary supplement, nutraceutical formulation, or pharmaceutical formulation. Compositions comprising C16:1n7-palmitoleate include dietary supplements, nutraceutical formulations, and pharmaceutical compositions. "Pharmaceutically acceptable composition" refers to a composition that is suitable for administration to a subject, particularly, a human. Such compositions include various excipients, diluents, carriers, and such other inactive agents well known to the skilled artisan. In another aspect, any of the pharmaceutical compositions, as described in the published U.S. Patent Application US 2012/0225941, incorporated herein by reference in its entirety, are provided where the pharmaceutical compositions include C16:1n7-palmitoleate or any derivatives thereof.

The methods described herein utilize compositions that include C16:1n7-palmitoleate or any one or more derivatives thereof as described in the U.S. Pat. No. 8,703,818, which is incorporated herein by reference in its entirety. In some embodiments, the C16:1n7-palmitoleate derivative is C16:1n7-palmitoleic acid. In further embodiments, the C16:1n7-palmitoleate derivative is cis-C16:1n7-palmitoleic acid. In some embodiments, the C16:1n7-palmitoleate derivative is a metal salt (e.g., $Na^+$, $K^+$, or $Li^+$) of cis-C16:1n7-palmitoleate. In further embodiments, the C16:1n7-palmitoleate derivative is an ester (e.g., ($C_1$-$C_8$) alkyl ester, methyl, ethyl, propyl, monoglyceride, diglyceride, triglyceride, or a combination thereof) of cis-C16:1n7-palmitoleate. In further embodiments, the C16:1n7-palmitoleate derivative is a methyl ester, ethyl ester, propyl ester of cis-C16:1n7-palmitoleate. In one embodiment, the cis-C16:1n7-palmitoleate ester is the ethyl ester.

The methods described herein are not limited to any particular chemical form of C16:1n7-palmitoleate and the compound may be given to subjects either as an ester, free acid or as a pharmaceutically acceptable salt.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease or medical condition, a positive control (a compound or composition known to exhibit the desired therapeutic effect) or a negative control (a subject or a sample that does not receive the therapy or receives a placebo) is typically employed.

As used herein, the term "effective amount" refers to a quantity sufficient to achieve a desired therapeutic and/or prophylactic effect, e.g., an amount which results in the prevention of, or decrease in joint discomfort. In the context of therapeutic or prophylactic applications, the amount of a composition administered to the subject will depend on the degree, type and severity of the disease or medical condition and on the characteristics of the individual, such as general health, age, sex, body weight and tolerance to drugs. Many different conditions can lead to joint discomfort, including osteoarthritis, rheumatoid arthritis, bursitis, gout, strains, sprains, and other injuries. The skilled artisan will be able to determine appropriate dosages depending on these and other factors. The compositions can also be administered in combination with one or more additional therapeutic compounds. In the methods described herein, C16:1n7-palmitoleate (or derivatives, pharmaceutically acceptable salts, or a combination thereof) may be administered to a subject having one or more signs or symptoms of joint discomfort. For example, a "therapeutically effective amount" of C16:

1n7-palmitoleate (or derivatives, pharmaceutically acceptable salts, or a combination thereof) means levels at which the physiological effects of the disease or medical condition giving rise to joint discomfort are, at a minimum, ameliorated. A therapeutically effective amount can be given in one or more administrations. In some embodiments, signs, symptoms or complications of a disease or medical condition leading to joint discomfort include, but are not limited to: impaired range of joint motion, increased joint pain, and reduced physical activity.

As used herein, "health-related quality of life" refers to the impact of a disease or medical condition on functional health status and well-being as perceived and reported by the subject.

As used herein, the term "monoglyceride" refers to a fatty acid chain, such as C16:1n7-palmitoleate, covalently bonded to a glycerol molecule through an ester linkage. As used herein, the term "diglyceride" refers to a fatty acid chain, such as C16:1n7-palmitoleate, covalently bonded to a glycerol molecule through an ester linkage, wherein the glycerol molecule is further bonded to one additional fatty acid chain, which may or may not be C16:1n7-palmitoleate, though one additional ester linkage. As used herein, the term "triglyceride" refers to a fatty acid chain, such as C16:1n7-palmitoleate, covalently bonded to a glycerol molecule through an ester linkage, wherein the glycerol molecule is further bonded to two additional fatty acid chains, either or both of which may or may not be C16:1n7-palmitoleate, though two additional ester linkages.

As used herein, the term "physical activity" includes flexibility or strengthening exercises, walking, swimming, aquatic exercises, running, cycling, and aerobic exercises such as the treadmill, Stairmaster etc. When measuring physical activity, it is necessary to consider the frequency, intensity, time, and type of the physical activity. Physical activities are classified as 'moderate,' 'hard,' or 'very hard' with respect to intensity. If an activity seems to be about as strenuous to the subject as walking at a normal pace, then the activity should be classified as moderate. If an activity seems to be about as strenuous to the subject as running, then the activity should be classified as very hard. If an activity seems harder than walking yet less strenuous than running, then the activity should be classified as hard. The physical activity can be performed intermittently or continuously during a given segment of the day, i.e., morning, afternoon, or evening. Strength exercises include pushups, pull-ups, sit-ups, lifting free weights, and Nautilus machine weight training, and flexibility activities include holding stretches for several seconds as well as yoga. An activity is classified as strength and flexibility only if it is planned exercise and the subjects' intention is to increase their strength or flexibility.

As used herein, "prevention" or "preventing" of a disorder or condition refers to one or more compounds that, in a statistical sample, reduces the occurrence of the disorder or condition in the treated sample relative to an untreated control sample, or delays the onset of one or more symptoms of the disorder or condition relative to the untreated control sample.

As used herein, the term "simultaneous" therapeutic use refers to the administration of at least two active ingredients by the same route and at the same time or at substantially the same time.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the terms "subject," "individual," or "patient" can be an individual organism, a vertebrate, a mammal, or a human.

As used herein, the term "therapeutic use" of the compounds discussed herein is defined as using one or more of the compounds discussed herein to treat or prevent a disease or medical condition implicating joint discomfort.

"Treating" or "treatment" as used herein covers the treatment of a disease or medical condition described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or medical condition.

It is also to be appreciated that the various modes of treatment or prevention of medical diseases and conditions as described are intended to mean "substantial," which includes total but also less than total treatment or prevention, and wherein some biologically or medically relevant result is achieved. The treatment may be a continuous prolonged treatment for a chronic disease or a single, or few time administrations for the treatment of an acute condition.

General

The presence of joint pain during strenuous exercise may indicate possible joint problems. Joint health is essential in aiding the proper functioning of the musculoskeletal system. Movable joints include cartilage which reduces friction, and the synovial membrane which is composed of cells that produce the synovial fluid that lubricates the joint. The cartilage and synovial membrane act as shock absorbers and allow bones to glide against each other, preventing direct contact and subsequent pain during movement.

Human joints are susceptible to degeneration from disease, trauma, and long-term repetitive use, which can eventually lead to pain. Pain can originate from bone, joints, ligaments, muscles, nerves and intervertebral disks, as well as other paravertebral tissues. A popular theory within the orthopedic community is that joint pain, such as that found in the knee or hip, results from bone-on-bone contact or inadequate cartilage cushioning. These conditions may frequently result from the progression of osteoarthritis, which is measured in terms of narrowing of the joint space.

Joint discomfort is most commonly caused by inflammation. Joint injury or short-term muscle overuse such as strenuous exercise can set off localized inflammation in the cartilage, ligaments, tendons, or bursae. Extracellular matrix (ECM) breakdown occurs when normal cartilage cells undergo exhaustive mechanical stimulation. This is evidenced by the upregulation of metalloproteinases (MMPs), a family of proteins that cleave the protein components of the ECM, and tumor necrosis factor (TNF)-alpha. During inflammation, nerves within the joints become sensitized to mechanical stimuli, which may lead to decreased joint mobility, increased joint stiffness, and increased joint discomfort.

C16:1n7-Palmitoleate Compositions

In some embodiments, the composition includes C16: 1n7-palmitoleate, or derivatives, pharmaceutically acceptable salts, or a combination thereof. Compositions that include C16:1n7-palmitoleate and its derivatives to be utilized in the methods described herein include any of those described in U.S. Pat. No. 8,703,818 which is incorporated herein by reference in its entirety.

In some embodiments, the composition utilized by the methods described herein, such as a nutraceutical, pharmaceutical, or a dietary supplement, comprises about 1% to about 100% of C16:1n7-palmitoleate and its derivatives relative to all of the components of the composition. In some embodiments, the composition comprises from about 5% to about 20%, from about 20% to about 30%, or at least about 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of C16:1n7-palmitoleate or one or more derivatives thereof relative to all of the components of the composition.

In some embodiments, the composition comprises a C16: 1n7-palmitoleate derivative, wherein the wt % of the C16: 1n7-palmitoleate derivative exceeds the wt % of any other single ingredient in the composition. In some embodiments, the composition comprises at least about 50 wt % of the C16:1n7-palmitoleate derivative. In some embodiments, the composition comprises at least about 60 wt % of the C16:1n7-palmitoleate derivative. In some embodiments, the composition comprises at least about 70 wt % of the C16:1n7-palmitoleate derivative. In some embodiments, the composition comprises at least about 80 wt % of the C16:1n7-palmitoleate derivative. In some embodiments, the composition comprises at least about 90 wt % of the C16:1n7-palmitoleate derivative.

Additionally or alternatively, in some embodiments, the composition, such as a nutraceutical, pharmaceutical, or a dietary supplement, comprises about 1% to about 100% of C16:1n7-palmitoleate and its derivatives relative to all of the fatty acids and fatty acid derivatives that are present in the composition. In some embodiments, the composition comprises from about 5% to about 20%, from about 20% to about 30%, or at least about 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of C16:1n7-palmitoleate or one or more derivatives thereof relative to all of the fatty acids and fatty acid derivatives that are present in the composition.

In certain embodiments, the composition, such as a nutraceutical, pharmaceutical, or a dietary supplement, comprises C16:1n7-palmitoleate and its derivatives and further comprises C16:0-palmitate and its derivatives. In certain embodiments, the composition comprises C16:1n7-palmitoleate and its derivatives relative to C16:0-palmitate and its derivatives in a ratio in excess of 1:1. In certain embodiments, the composition comprises a ratio of C16:1n7-palmitoleate and its derivatives relative to C16:0-palmitate and its derivatives (i.e., palmitoleate:palmitate), wherein the ratio is about 1.1:1, 1.2:1, 1.3:1, 1.4:1, 1.5:1, 1.6:1, 1.7:1, 1.8:1, 1.9:1, 2.0:1, 2.1:1, 2.2:1, 2.3:1, 2.4:1, 2.5:1, 2.6:1, 2.7:1, 2.8:1, 2.9:1, 3.0:1, 3.1:1, 3.2:1, 3.3:1, 3.4:1, 3.5:1, 3.6:1, 3.7:1, 3.8:1, 3.9:1, 4.0:1, 4.1:1, 4.2:1, 4.3:1, 4.4:1, 4.5:1, 4.6:1, 4.7:1, 4.8:1, 4.9:1, 5.0:1, 5.1:1, 5.2:1, 5.3:1, 5.4:1, 5.5:1, 5.6:1, 5.7:1, 5.8:1, 5.9:1, 6.0:1, 6.1:1, 6.2:1, 6.3:1, 6.4:1, 6.5:1, 6.6:1, 6.7:1, 6.8:1, 6.9:1, 7.0:1, 7.1:1, 7.2:1, 7.3:1, 7.4:1, 7.5:1, 7.6:1, 7.7:1, 7.8:1, 7.9:1, 8.0:1, 8.1:1, 8.2:1, 8.3:1, 8.4:1, 8.5:1, 8.6:1, 8.7:1, 8.8:1, 8.9:1, 9.0:1, 9.1:1, 9.2:1, 9.3:1, 9.4:1, 9.5:1, 9.6:1, 9.7:1, 9.8:1, 9.9:1, 10.0:1, 11:1, 12:1, 13:1, 14:1, 15:1, 16:1, 17:1, 18:1, 19:1, 20:1, 25:1, 30:1, 35:1, 40:1, 45:1, 50:1, 55:1, 60:1, 65:1, 70:1, 75:1, 80:1, 85:1, 90:1, 95:1, 100:1, 200:1 or a ratio between any two of those recited above.

In some embodiments, the composition comprises a C16: 1n7-palmitoleate derivative and a palmitate derivative, wherein the ratio of the C16:1n7-palmitoleate derivative to the palmitate derivative (i.e., palmitoleate:palmitate) is from about 12:1 to about 100:1; and each palmitoleate and palmitate derivative is independently selected from the group consisting of a free acid, pharmaceutically acceptable salt, ($C_1$-$C_8$) alkyl ester, monoglyceride, diglyceride, triglyceride and a combination thereof. In some embodiments, the ratio of the C16:1n7-palmitoleate derivative to the palmitate derivative is from about 15:1 to about 50:1. In some embodiments, the ratio of the C16:1n7-palmitoleate derivative to the palmitate derivative is from about 50:1 to about 100:1.

In some embodiments, all of the palmitoleate and palmitate derivatives are ($C_1$-$C_8$) alkyl esters. In some embodiments, all of the palmitoleate and palmitate derivatives are ethyl esters. In some embodiments, all of the palmitoleate and palmitate derivatives are methyl esters. In some embodiments, all of the palmitoleate and palmitate derivatives are propyl, butyl, pentyl, hexyl, heptyl or octyl esters. In some embodiments, all of the palmitoleate and palmitate derivatives are free acids or pharmaceutically acceptable salts thereof. In some embodiments, all of the palmitoleate and palmitate derivatives are selected from the group consisting of monoglycerides, diglycerides, triglycerides and combinations thereof. In some embodiments, the C16:1n7-palmitoleate derivative is a cis-C16:1n7-palmitoleate derivative.

In certain embodiments, the composition, such as a nutraceutical, pharmaceutical, or a dietary supplement, comprises C16:1n7-palmitoleate and its derivatives and further comprises C18:1n9-oleate or its derivatives. In certain embodiments, the composition comprises C16:1n7-palmitoleate and its derivatives relative to C18:1n9-oleate and its derivatives in a ratio in excess of 1:1.

In some embodiments, the composition, such as a nutraceutical, pharmaceutical, or a dietary supplement, comprises C16:1n7-palmitoleate and its derivatives and further comprises C18:1n9-oleate and its derivatives, wherein the ratio of the C16:1n7-palmitoleate derivative to the oleate derivative (i.e., palmitoleate:oleate) is from about 1.1:1 to about 100:1. In some embodiments, the composition comprises a ratio of C16:1n7-palmitoleate and its derivatives relative to C18:1n9-oleate and its derivatives (i.e., palmitoleate:oleate), wherein the ratio is about 1.1:1, 1.2:1, 1.3:1, 1.4:1, 1.5:1, 1.6:1, 1.7:1, 1.8:1, 1.9:1, 2.0:1, 2.1:1, 2.2:1, 2.3:1, 2.4:1, 2.5:1, 2.6:1, 2.7:1, 2.8:1, 2.9:1, 3.0:1, 3.1:1, 3.2:1, 3.3:1, 3.4:1, 3.5:1, 3.6:1, 3.7:1, 3.8:1, 3.9:1, 4.0:1, 4.1:1, 4.2:1, 4.3:1, 4.4:1, 4.5:1, 4.6:1, 4.7:1, 4.8:1, 4.9:1, 5.0:1, 5.1:1, 5.2:1, 5.3:1, 5.4:1, 5.5:1, 5.6:1, 5.7:1, 5.8:1, 5.9:1, 6.0:1, 6.1:1, 6.2:1, 6.3:1, 6.4:1, 6.5:1, 6.6:1, 6.7:1, 6.8:1, 6.9:1, 7.0:1, 7.1:1, 7.2:1, 7.3:1, 7.4:1, 7.5:1, 7.6:1, 7.7:1, 7.8:1, 7.9:1, 8.0:1, 8.1:1, 8.2:1, 8.3:1, 8.4:1, 8.5:1, 8.6:1, 8.7:1, 8.8:1, 8.9:1, 9.0:1, 9.1:1, 9.2:1, 9.3:1, 9.4:1, 9.5:1, 9.6:1, 9.7:1, 9.8:1, 9.9:1, 10.0:1, 11:1, 12:1, 13:1, 14:1, 15:1, 16:1, 17:1, 18:1, 19:1, 20:1, 25:1, 30:1, 35:1, 40:1, 45:1, 50:1, 55:1, 60:1, 65:1, 70:1, 75:1, 80:1, 85:1, 90:1, 95:1, 100:1, 200:1 or a ratio between any two of those recited above.

In certain embodiments, the composition further comprises an oleate derivative, wherein the ratio of the C16:1n7-palmitoleate derivative to the oleate derivative is from about 6:1 to about 100:1, and each oleate derivative is independently selected from the group consisting of a free acid, pharmaceutically acceptable salt, ($C_1$-$C_8$) alkyl ester, monoglyceride, diglyceride, triglyceride and a combination thereof. In certain embodiments, the ratio of the C16:1n7-palmitoleate derivative to the oleate derivative is from about 10:1 to about 20:1. In certain embodiments, the ratio of the C16:1n7-palmitoleate derivative to the oleate derivative is from about 20:1 to about 50:1. In certain embodiments, the ratio of the C16:1n7-palmitoleate derivative to the oleate derivative is from about 50:1 to about 100:1.

Additionally or alternatively, in any of the above embodiments, the composition, such as a nutraceutical, pharmaceutical, or a dietary supplement, comprises C16:1n7-palmitoleate and its derivatives and further comprises C18:1n7-vaccenoate or its derivatives. In certain embodiments, the composition comprises C16:1n7-palmitoleate and its derivatives relative to C18:1n7-vaccenoate and its derivatives in a ratio in excess of 1:1. In some embodiments, the composition comprises a ratio of C16:1n7-palmitoleate and its derivatives relative to C18:1n7-vaccenoate and its derivatives (i.e., palmitoleate:C18:1n7-vaccenoate), wherein the ratio is in excess of 1.1:1, 1.2:1, 1.3:1, 1.4:1, 1.5:1, 1.6:1, 1.7:1, 1.8:1, 1.9:1, 2.0:1, 2.1:1, 2.2:1, 2.3:1, 2.4:1, 2.5:1, 2.6:1, 2.7:1, 2.8:1, 2.9:1, 3.0:1, 3.1:1, 3.2:1, 3.3:1, 3.4:1, 3.5:1, 3.6:1, 3.7:1, 3.8:1, 3.9:1, 4.0:1, 4.1:1, 4.2:1, 4.3:1, 4.4:1, 4.5:1, 4.6:1, 4.7:1, 4.8:1, 4.9:1, 5.0:1, 5.1:1, 5.2:1, 5.3:1, 5.4:1, 5.5:1, 5.6:1, 5.7:1, 5.8:1, 5.9:1, 6.0:1, 6.1:1, 6.2:1, 6.3:1, 6.4:1, 6.5:1, 6.6:1, 6.7:1, 6.8:1, 6.9:1, 7.0:1, 7.1:1, 7.2:1, 7.3:1, 7.4:1, 7.5:1, 7.6:1, 7.7:1, 7.8:1, 7.9:1, 8.0:1, 8.1:1, 8.2:1, 8.3:1, 8.4:1, 8.5:1, 8.6:1, 8.7:1, 8.8:1, 8.9:1, 9.0:1, 9.1:1, 9.2:1, 9.3:1, 9.4:1, 9.5:1, 9.6:1, 9.7:1, 9.8:1, 9.9:1, 10.0:1, 11:1, 12:1, 13:1, 14:1, 15:1, 16:1, 17:1, 18:1, 19:1, 20:1, 25:1, 30:1, 35:1, 40:1, 45:1, 50:1, 55:1, 60:1, 65:1, 70:1, 75:1, 80:1, 85:1, 90:1, 95:1, or 100:1.

In certain embodiments, the composition further comprises a C18:1n7-vaccenoate derivative, wherein the ratio of the C16:1n7-palmitoleate derivative to the C18:1n7-vaccenoate derivative is from about 3:1 to about 100:1, and each C18:1n7-vaccenoate derivative is independently selected from the group consisting of a free acid, pharmaceutically acceptable salt, ($C_1$-$C_8$) alkyl ester, monoglyceride, diglyceride, triglyceride and a combination thereof. In certain embodiments, the ratio of the C16:1n7-palmitoleate derivative to the C18:1n7-vaccenoate derivative is from about 5:1 to about 20:1. In certain embodiments, the ratio of the C16:1n7-palmitoleate derivative to the C18:1n7-vaccenoate derivative is from about 20:1 to about 50:1. In certain embodiments, the ratio of the C16:1n7-palmitoleate derivative to the C18:1n7-vaccenoate derivative is from about 50:1 to about 100:1.

In another embodiment, a composition contains not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight, palmitic acid, if any. In another embodiment, a composition contains substantially no palmitic acid. In still another embodiment, a composition contains no palmitic acid and/or derivative thereof.

C16:1n7-palmitoleate and derivatives thereof, for use in the methods described herein, can be obtained from any of the sources and methods described in U.S. Pat. No. 8,703,818, which is incorporated herein by reference in its entirety. In certain embodiments, C16:1n7-palmitoleate and derivatives thereof are isolated, concentrated, and/or purified from a source selected from the group consisting of one or more plants, animals, fish, and microorganisms. In other embodiments, the C16:1n7-palmitoleate moiety of the C16:1n7-palmitoleate derivative is obtained from a source selected from the group consisting of fish, macadamia nuts, sea buckthorn, tallow, algae, bacteria, yeast, and a combination thereof.

In some embodiments, the C16:1n7-palmitoleate derivative comprises a C16:1n7-palmitoleate moiety that is obtained from fish. In some embodiments, the fish is selected from the group consisting of anchovies, menhaden, pollock, herring, cod, salmon, smelt, tuna, mackerel, krill and a combination thereof. In some embodiments, the fish comprise anchovies. In other embodiments, the fish comprise menhaden.

Methods for Preventing or Treating Joint Discomfort

The present technology provides methods for preventing or treating joint discomfort in a subject comprising administering to the subject an effective amount of a composition comprising C16:1n7-palmitoleate, derivatives thereof, pharmaceutically acceptable salts thereof, or a combination thereof. In some embodiments, the method includes administering to the subject one or more of any one of the above embodiments of the composition.

The compositions comprising C16:1n7-palmitoleate, derivatives thereof, pharmaceutically acceptable salts thereof, or a combination thereof described herein are useful to prevent or treat joint discomfort.

Compositions comprising C16:1n7-palmitoleate, derivatives thereof, pharmaceutically acceptable salts thereof, or a combination thereof, such as those described above, (e.g., C16:1n7-palmitoleate alone or C16:1n7-palmitoleate combined with C18:1n9-oleate) are useful in treating joint discomfort, as well as the signs, symptoms or complications of joint discomfort.

The disclosure also provides for both prophylactic and therapeutic methods of treating a subject having or at risk for (or susceptible to) joint discomfort. Accordingly, the present methods provide for the prevention and/or treatment of joint discomfort in a subject by administering an effective amount of a compositions comprising C16:1n7-palmitoleate, derivatives thereof, pharmaceutically acceptable salts thereof, or a combination thereof to a subject in need thereof.

Therapeutic Methods

One aspect of the present technology includes methods of treating joint discomfort in a subject in need thereof. One aspect of the present technology includes methods of treating joint discomfort in a subject diagnosed as having, suspected as having, or at risk of having, joint discomfort. In therapeutic applications, compositions or medicaments comprising C16:1n7-palmitoleate, derivatives thereof, pharmaceutically acceptable salts thereof, or a combination thereof are administered to a subject suspected of, or already suffering from joint discomfort in an amount sufficient to cure, or at least partially arrest, the symptoms of the disease or medical condition, including its complications and intermediate pathological phenotypes in development of the disease or medical condition.

Subjects suffering from joint discomfort can be identified by any or a combination of diagnostic or prognostic assays known in the art. For example, typical symptoms of joint discomfort include, but are not limited to, symptoms such as, e.g., impaired range of joint motion, increased joint pain, and reduced physical activity.

In some embodiments, the subject may exhibit impaired range of joint motion, increased joint pain, and/or reduced physical activity, which are measurable using techniques known in the art.

Prophylactic Methods

In one aspect, the present technology provides a method for preventing or delaying the onset of joint discomfort or symptoms of joint discomfort in a subject in need thereof. Subjects at risk for joint discomfort can be identified by, e.g., any or a combination of diagnostic or prognostic assays known in the art. In prophylactic applications, compositions or medicaments comprising C16:1n7-palmitoleate, derivatives thereof, pharmaceutically acceptable salts thereof, or a combination thereof are administered to a subject susceptible to, or otherwise at risk for joint discomfort in an amount sufficient to eliminate or reduce the risk, or delay the outset of joint discomfort, including biochemical, histologic and/or behavioral symptoms of the disease or disorder, its complications and intermediate pathological phenotypes presenting during development of the disease. Administration of a prophylactic compositions or medicaments comprising C16:1n7-palmitoleate, its derivatives, pharmaceutically acceptable salts thereof, or a combination thereof can occur prior to the manifestation of symptoms characteristic of the disease or disorder, such that the disease or disorder is prevented or, alternatively, delayed in its progression.

Subjects at risk for joint discomfort may exhibit one or more of the following non-limiting risk factors: arthritis, unusual exertion or overuse of joints, strains or sprains, fractures, bursitis, viral infections, chondromalacia patella, and synovial impingement.

For therapeutic and/or prophylactic applications, a composition comprising one or more of C16:1n7-palmitoleate, a C16:1n7-palmitoleate derivative, or a pharmaceutically acceptable salt thereof, is administered to the subject. In some embodiments, the composition is administered one, two, three, four, or five times per day. In some embodiments, the composition is administered more than five times per day. Additionally or alternatively, in some embodiments, the composition is administered every day, every other day, every third day, every fourth day, every fifth day, or every sixth day. In some embodiments, the composition is administered weekly, bi-weekly, tri-weekly, or monthly. In some embodiments, the composition is administered for a period of one, two, three, four, or five weeks. In some embodiments, the composition is administered for six weeks or more. In some embodiments, the composition is administered for twelve weeks or more. In some embodiments, the composition is administered for a period of less than one year. In some embodiments, the composition is administered for a period of more than one year.

In some embodiments, the composition is administered daily for one week or more. In some embodiments, the composition is administered daily for 2 weeks or more. In some embodiments, the composition is administered daily for 3 weeks or more. In some embodiments, the composition is administered daily for 4 weeks or more. In some embodiments, the composition is administered daily for 6 weeks or more. In some embodiments, the composition is administered daily for 12 weeks or more.

Use of C16:1n7-Palmitoleate to Prevent, Ameliorate or Treat Joint Discomfort

In one aspect, the present technology provides a method for improving joint function in a subject in need thereof comprising administering to the subject an effective amount of a composition comprising one or more of C16:1n7-palmitoleate, a C16:1n7-palmitoleate derivative, or a pharmaceutically acceptable salt thereof. In some embodiments of the method, the composition also includes C16:0-palmitate, a C16:0-palmitate derivative, or a combination thereof. Additionally or alternatively, in some embodiments of the method, the composition also includes C18:1n9-oleate, a C18:1n9-oleate derivative, or a combination thereof.

In some embodiments of the method, the subject experiences joint pain while engaging in moderate, hard, or very hard physical activity. In certain embodiments, the subject is human. In some embodiments of the method, the affected joint is the knee, shoulder, elbow, forearm, wrist, hip, ankle, or foot.

Physical activity includes flexibility or strengthening exercises, walking, swimming, aquatic exercises, running, cycling, and aerobic exercises such as the treadmill, Stairmaster etc. Physical activities are classified as 'moderate,' 'hard,' or 'very hard' with respect to intensity. If an activity seems to be about as strenuous to the subject as walking at a normal pace, then the activity is classified as moderate. If an activity seems to be about as strenuous to the subject as running, then the activity is classified as very hard. If the subject regards an activity as more strenuous than walking yet less strenuous than running, then the activity is classified as hard. The physical activity can be performed intermittently or continuously during a segment of the day, i.e., morning, afternoon, or evening. Strength exercises include pushups, pull-ups, sit-ups, lifting free weights, and Nautilus machine weight training, and flexibility activities include holding stretches for several seconds as well as yoga. An activity is classified as strength and flexibility only if it is planned exercise and the subjects' intention is to increase their strength or flexibility. In other embodiments, the occurrence of the subject's joint discomfort is not induced by physical activity.

In some embodiments, administration of the composition causes an increase in the time of onset of maximum discomfort or pain level in the subject. In some embodiments, the time of onset of maximum discomfort or pain level in the subject is increased by at least 20%. In some embodiments, the time of onset of maximum discomfort or pain level in the subject is increased by at least 30%. In some embodiments, the time of onset of maximum discomfort or pain level in the subject is increased by at least 50%. In some embodiments, the time of onset of maximum discomfort or pain level in the subject is increased by at least 75%.

In some embodiments, the time of onset of maximum discomfort or pain level in the subject is increased within one week following the administration of the composition to the subject. In some embodiments, the time of onset of maximum discomfort or pain level in the subject is increased by at least 20% within one week following the administration of the composition to the subject.

In some embodiments, the time of onset of maximum discomfort or pain level in the subject is increased within one month following the administration of the composition to the subject. In some embodiments, the time of onset of maximum discomfort or pain level in the subject is increased by at least 30% within one month following the administration of the composition to the subject.

In some embodiments, administration of the composition causes an increase in the range of joint motion in the subject. In some embodiments, the range of joint motion is increased by at least 10%.

In some embodiments of the method, the range of joint motion is increased within one month following the administration of the composition to the subject. In some embodiments of the method, the range of joint motion is increased within three weeks following the administration of the composition to the subject. In some embodiments of the method, the range of joint motion is increased within two weeks following the administration of the composition to the subject. In some embodiments of the method, the range of joint motion is increased within one week following the administration of the composition to the subject.

In some embodiments, the range of joint motion is increased by at least 10% within one month following the administration of the composition to the subject.

Modes of Administration and Effective Dosages

Any method known to those in the art for contacting a cell, organ or tissue with the compositions of the present technology (i.e., C16:1n7-palmitoleate or derivatives or pharmaceutically acceptable salts thereof) may be employed. Suitable methods include in vitro, ex vivo, or in vivo methods. In vivo methods typically include the administration of C16:1n7-palmitoleate or derivatives or pharmaceutically acceptable salts thereof, such as those described above, to a mammal, suitably a human. When used in vivo for therapy, C16:1n7-palmitoleate or derivatives or pharmaceutically acceptable salts thereof may be administered to the subject in effective amounts (i.e., amounts that have desired therapeutic effects). The dose and dosage regimen will depend upon the degree of the medical condition in the subject, the characteristics of C16:1n7-palmitoleate or derivatives or pharmaceutically acceptable salts thereof, e.g., its therapeutic index, the subject, and the subject's history.

The effective amount may be determined during pre-clinical trials and clinical trials by methods familiar to physicians and clinicians. An effective amount of C16:1n7-palmitoleate (or derivatives or pharmaceutically acceptable salts thereof) useful in the methods may be administered to a mammal in need thereof by any of a number of well-known methods for administering pharmaceutical compounds. C16:1n7-palmitoleate (or derivatives or pharmaceutically acceptable salts thereof) may be administered systemically or locally.

C16:1n7-palmitoleate (or derivatives thereof) may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucuronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the salt is an acetate, tartrate or trifluoroacetate salt.

C16:1n7-palmitoleate or derivatives or pharmaceutically acceptable salts thereof described herein can be incorporated into pharmaceutical compositions for administration, alone or in combination, to a subject for the treatment or prevention of joint pain. Such compositions typically include the active agent (e.g., C16:1n7-palmitoleate) and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

Compositions containing C16:1n7-palmitoleate (or derivatives or pharmaceutically acceptable salts thereof) can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, isotonic agents are included, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active compound plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, C16:1n7-palmitoleate (or derivatives or pharmaceutically acceptable salts thereof) can be delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of C16:1n7-palmitoleate (or derivatives or pharmaceutically acceptable salts thereof) as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

C16:1n7-palmitoleate (or derivatives or pharmaceutically acceptable salts thereof) can be formulated in a carrier system. The carrier can be a colloidal system. The colloidal system can be a liposome, a phospholipid bilayer vehicle. One skilled in the art would appreciate that there are a variety of methods to prepare liposomes. See Lichtenberg, et al., *Methods Biochem. Anal.*, 33:337-462 (1988); Anselem, et al., *Liposome Technology*, CRC Press (1993)). Liposomal formulations can delay clearance and increase cellular uptake (See Reddy, *Ann. Pharmacother.*, 34(7-8):915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, C16:1n7-palmitoleate (or derivatives or pharmaceutically acceptable salts thereof) can be embedded in the polymer matrix. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.).

In some embodiments, C16:1n7-palmitoleate (or derivatives or pharmaceutically acceptable salts thereof) are prepared with carriers that will protect C16:1n7-palmitoleate (or derivatives or pharmaceutically acceptable salts thereof) against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811. C16:1n7-palmitoleate (or derivatives or pharmaceutically acceptable salts thereof) can also be formulated to enhance intracellular delivery.

Dosage, toxicity and therapeutic efficacy of C16:1n7-palmitoleate (or derivatives or pharmaceutically acceptable salts thereof) can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In some embodiments, C16:1n7-palmitoleate, or derivatives or pharmaceutically acceptable salts thereof, exhibit high therapeutic indices.

The dosage of such compounds lies within a range of circulating concentrations that include the ED50 with little or no toxicity. The dosage may vary within this range depending upon the dosage form employed and the route of administration utilized. For C16:1n7-palmitoleate (or derivatives or pharmaceutically acceptable salts thereof) used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

Typically, an effective amount of C16:1n7-palmitoleate (or derivatives or pharmaceutically acceptable salts thereof), sufficient for achieving a therapeutic or prophylactic effect, ranges from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of C16:1n7-palmitoleate (or derivatives or pharmaceutically acceptable salts thereof) ranges from 0.001-10,000 micrograms per kg body weight. In one embodiment, C16:1n7-palmitoleate (or derivatives or pharmaceutically acceptable salts thereof) concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the medical condition is reduced or terminated, and until the subject shows partial or complete amelioration of symptoms of the medical condition. Thereafter, the patient can be administered a prophylactic regime.

In some embodiments, a therapeutically effective amount of C16:1n7-palmitoleate (or derivatives or pharmaceutically acceptable salts thereof) may be defined as a concentration of C16:1n7-palmitoleate (or derivatives or pharmaceutically acceptable salts thereof) at the target tissue of $10^{-12}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue. In some embodiments, the doses are administered by single daily or weekly administration, but may also include continuous administration (e.g., parenteral infusion or transdermal application). In some embodiments, the dosage of C16:1n7-palmitoleate (or derivatives or pharmaceutically acceptable salts thereof) is provided at a "low," "mid," or "high" dose level. In one embodiment, the low dose is provided from about 0.0001 to about 0.5 mg/kg/h, suitably from about 0.001 to about 0.1 mg/kg/h. In one embodiment, the mid-dose is provided from about 0.01 to about 1.0 mg/kg/h, suitably from about 0.01 to about 0.5 mg/kg/h. In one embodiment, the high dose is provided from about 0.5 to about 10 mg/kg/h, suitably from about 0.5 to about 2 mg/kg/h.

In some embodiments, C16:1n7-palmitoleate, or derivatives or pharmaceutically acceptable salts thereof, are administered in an amount that achieves a serum concentration of about 100 ng/ml to about 9000 ng/ml. In another embodiment, C16:1n7-palmitoleate, or derivatives or pharmaceutically acceptable salts thereof, are administered in an amount that achieves a serum concentration of about 100 ng/ml to about 1000 ng/ml. In other embodiments, the serum concentration achieved is about 300 ng/ml to about 500 ng/ml, about 100 ng/ml to about 500 ng/ml, about 500 ng/ml to about 1000 ng/ml, about 1000 ng/ml to about 1500 ng/ml, about 500 ng/ml to about 1500 ng/ml, about 1000 ng/ml to about 2000 ng/ml, about 1500 ng/ml to about 2000 ng/ml, about 2000 ng/ml to about 3000 ng/ml, about 2000 ng/ml to about 2500 ng/ml, about 2500 ng/ml to about 3000 ng/ml, about 3000 ng/ml to about 4000 ng/ml, about 3000 ng/ml to about 3500 ng/ml, about 3500 ng/ml to about 4000 ng/ml, about 4000 ng/ml to about 5000 ng/ml, about 4000 ng/ml to about 4500 ng/ml, about 4500 ng/ml to about 5000 ng/ml, about 5000 ng/ml to about 6000 ng/ml, about 5000 ng/ml to about 5500 ng/ml, about 5500 ng/ml to about 6000 ng/ml, about 6000 ng/ml to about 7000 ng/ml, about 7000 ng/ml to about 8000 ng/ml, or about 8000 ng/ml to about 9000 ng/ml.

The skilled artisan will appreciate that certain factors may influence the dosage and timing required to effectively treat a subject, including but not limited to, the severity of the medical disease or condition, previous treatments, the general health and/or age of the subject, and other diseases present. Moreover, treatment of a subject with a therapeutically effective amount of the therapeutic compositions described herein can include a single treatment or a series of treatments.

In some embodiments, C16:1n7-palmitoleate, or derivatives or pharmaceutically acceptable salts thereof, are formulated as a pharmaceutical composition within a soft gelatin capsule. In some embodiments, the soft gelatin capsule includes about 0.5 grams, about 1 gram, about 1.5 grams, or about 2 grams of the pharmaceutical composition comprising at least 20%, at least 30%, at least 40%, at least 50%, at least 60%, at least 70%, at least 80% or at least 90% of C16:1n7-palmitoleate, or a derivative or pharmaceutically acceptable salt thereof. In some embodiments, one capsule per day is administered to a subject for the treatment or prevention of any of the conditions, such as joint discomfort, as described herein. In some embodiments, two capsules per day are administered to the subject. In some embodiments, two to ten capsules per day are administered to the subject.

In some embodiments, the subject is a mammal, a reptile, or an amphibian. In some embodiments, the mammal is any mammal, including, for example, farm animals, such as sheep, pigs, cows, and horses; pet animals, such as dogs and cats; laboratory animals, such as rats, mice and rabbits. In some embodiments, the mammal is a human.

Combination Therapy with C16:1n7-Palmitoleate and Other Therapeutic Agents

In some embodiments, C16:1n7-palmitoleate, derivatives thereof, pharmaceutically acceptable salts thereof, or combinations thereof, may be combined with one or more additional therapeutic agents for the prevention or treatment of joint discomfort. By way of example, but not by way of limitation, treatment for joint discomfort, can include, in addition to C16:1n7-palmitoleate, derivatives thereof, pharmaceutically acceptable salts thereof, or combinations thereof, acetaminophen, ibuprofen, naproxen sodium, Cox-2 inhibitors, muscle relaxants, opioids, antidepressants, anti-epileptic drugs, topical agents (e.g., methyl salicylate, capsaicin), steroid injections, and hyaluronan injections.

In some embodiments, an additional therapeutic agent is administered to a subject in combination with C16:1n7-palmitoleate, its derivatives, pharmaceutically acceptable salts thereof, or combinations thereof, such that a synergistic therapeutic effect is produced. Therefore, lower doses of one or both of the therapeutic agents may be used in treating joint discomfort, resulting in increased therapeutic efficacy and decreased side-effects.

In any case, the multiple therapeutic agents may be administered in any order, e.g., sequentially or separately or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary between more than zero weeks to less than four weeks. In addition, the combination methods, compositions and formulations are not to be limited to the use of only two agents.

EXAMPLES

The present technology is further illustrated by the following examples, which should not be construed as limiting in any way. For each of the examples below, C16:1n7-palmitoleate or any derivatives thereof could be used.

Example 1 Methods for Evaluating the Effect of C16:1n7-Palmitoleate in Improving Joint Function in Human Subjects Healthy volunteers between the ages of 30 and 65 years, and with a BMI between 18 and 35 kg/m' were screened as potential candidates for the study. Subjects were recruited through online or database queries and were subsequently screened via phone interviews prior to scheduling a screening visit. Preliminary exclusion criteria for the study population included subjects with cardiopulmonary disease or a musculoskeletal disease that would interfere with their ability to perform the required functional assessments, as well as those with a history of arthritis or knee joint replacement.
Initial Screening Visit The study duration was thirty-seven (37) days with a total of 4 visits per subject. The initial screening visit (Visit 1) occurred 7 days prior to the initiation of the study (Day −7). Subjects arrived in the clinic having fasted for 10 hours in preparation for Visit 1. Subjects underwent the informed consent process and were screened for the presence of all the inclusion criteria and the absence of all the exclusion criteria. The screening process also included taking a detailed medical history, recording prior and concomitant medications, performing a physical examination, and documenting vital signs, and anthropometric measures. To determine eligibility, subjects continuously used the Stepmill at a set rate for 10 minutes until they complained of knee discomfort (in at least one knee) that scored at least 5 on an 11 point numeric pain rating scale. The time of onset of joint pain was recorded. Subjects were also instructed to inform the clinician when their discomfort began to subside and when their discomfort completely resolved.

Baseline Assessments for Joint Pain, Range of Motion, Activity Levels and Health-Related Quality of Life.

Baseline assessments included evaluating the pain or discomfort experienced by subjects during exercise testing. Subjects were instructed to exercise on a StepMill® model 7000PT (StairMaster® Health & Fitness Products, Inc., Kirkland, Wash.) at a set rate (Level 4) for 10 minutes. The following knee discomfort measures were recorded from the beginning of the Stepmill test: (1) time of onset of initial joint pain; (2) time of onset of maximum joint pain; (3) time at which initial improvement in knee joint pain was achieved; and (4) time of complete recovery from knee joint pain. Subjects that reported a discomfort level of 5 on an 11 point (0-10) Likert scale in at least one knee within the 10-minute period were selected. Once the requisite pain level was achieved, the subject was asked to continue stepping for an additional two minutes in order to record the maximum pain level reached before disembarking from the stepmill. Subjects who experienced a pain score of 5 (or greater) within one minute of starting the stress test were excluded.

Other performance-based physical functioning measures including the 6-Minute Timed Walk and Knee Range of Motion (ROM) were also performed by the subjects. In the 6-Minute Timed Walk, subjects walked up and down a hallway for 6 minutes and were instructed to walk as rapidly as possible within their comfort zone, and as rapidly as possible without causing themselves any pain.

Goniometry was used to measure knee range of motion. To measure Knee Extension, subjects were instructed to extend the left or right knee to full extension without changing the position of their pelvis and lumbar spine. An inclinometer was placed along the subject's shin so as to document the range of motion in degrees. To measure Knee Flexion, subjects were asked to lie on their stomach with their shins off the end of the table, and were instructed to fully extend their knees. The subject was then asked to actively flex his/her knee to a full flexion position. The following scales and questionnaires: Stanford Exercise Behavior Scale—Stretching and Aerobics, Knee-related QOL subscale of KOOS Knee Survey, SF-12, and Knee Discomfort Improvement Scale were completed by the subjects at the initial screening.

Subjects who presented with no knee joint pain at rest and no diagnosable markers indicative of active arthritis (outlined in the American College of Rheumatology (ACR) guidelines), and who scored 5 or more on the 11-point Likert Scale for pain within 10 minutes while performing the Stepmill Protocol during the initial screening visit, were selected as candidates for the randomized, double-blind, placebo-controlled study. Potential subjects reporting the occasional use of nonsteroidal anti-inflammatory drugs (NSAIDs), other pain relief medications, or anti-inflammatory supplements underwent a 2-week washout period before returning to the clinic for Visit 2 (Day 0).
Study Design The study was set up as a randomized, double-blind, placebo-controlled clinical trial. At Visit 2 (Day 0), the clinical staff interviewed the subjects to determine whether there were changes in the subjects' medical history or if the subjects started any new medications. The subjects also underwent adverse event review and compliance assessment.

Subjects who met all of the study inclusion criteria and none of the exclusion criteria were randomly assigned to either the C16:1n7-palmitoleate-treatment or placebo groups. The C16:1n7-palmitoleate composition included palmitoleic acid, gelatin, glycerin and purified water whereas the placebo included medium chain triglycerides. GC analysis demonstrated that the C16:1n7-palmitoleate composition contained at least 50% palmitoleic acid and less than 1% palmitic acid. The subjects and the clinical staff were unaware of what group a particular subject was allocated to. Baseline assessments for joint pain and knee range of motion in a subject were obtained via the 6-Minute Timed Walk, Stepmill Protocol, and goniometry. At the end of the visit, subjects were provided with a 7-day supply of the C16:1n7-palmitoleate composition or placebo and daily dosing diaries. Subjects were instructed to ingest a single capsule of the C16:1n7-palmitoleate composition or the placebo per day.

Subjects returned to the clinic at Visit 3 (Day 7) for repeat assessments of joint pain, range of motion, activity levels and health-related quality of life scores. After the performance-based physical functioning measures were evaluated, the subjects were provided with a 23-day supply of the C16:1n7-palmitoleate composition or placebo. Subjects returned to the clinic at Visit 4 (Day 30), which marked the end of the study, for reevaluation of the performance-based physical functioning measures.

Experimental Endpoints

Experimental endpoints included Change in Time of Onset and Offset of Discomfort, Changes in 6-Minute Timed Walk, Change in Knee Range of Motion as measured by goniometry including Left and Right Knee Extension and Left and Right Knee Flexion. Stanford Exercise Scale—Stretching and Aerobics was used to measure the effect of the C16:1n7-palmitoleate composition on physical activity levels.

Quality of life (QOL) was assessed using Change in SF-12 and Knee-related QOL subscale of KOOS Knee Survey, and Knee Discomfort Improvement Scale. The SF-12 is a multipurpose short form survey with 12 questions, all selected from the SF-36 Health Survey. The questions were combined, scored, and weighted to create two scales that provide glimpses into the subject's mental and physical functioning and overall health-related-quality of life. Physical and Mental Health Component Summary Scores were computed using the scores of the twelve questions and a range from 0 to 100, where zero corresponds to the lowest level of health measured by the scales and 100 corresponds to the highest level of health.

Knee injury and Osteoarthritis Outcome Score (KOOS) is an instrument to assess the patients' opinion about their knee and knee-associated problems. For this study, only the Knee Related QOL subscale was used.

Knee Discomfort Improvement Scale refers to the response to the question "Is your overall knee discomfort improving?", rated using a 3-point scale where zero is "Not at All", 1 is "Moderately" and 2 is "Definitely".

The safety of the C16:1n7-palmitoleate composition was determined via Adverse Events Analysis.

Statistical Analysis

Parallel dual data entries were completed by data management personnel across all endpoints. Data validation and reconciliation of parallel entries occurred after the dual data entry process. The monitoring team compared the values on the original CRFs or source documents, correcting any identified discrepancies.

All data elements were screened for coherency (reasonableness), and all missing, suspicious, or impossible values were referred back to the monitoring team for query generation and resolution. The database was formally locked after all suspicious entries in the database were resolved. The product assignments were then distinguished from the randomization or blinding codes and merged into the database and data tables.

All variables under investigation were summarized by time point. Endpoints in interval/ratio scale were presented as (n, mean, standard deviation and standard error). Numerical variables were also presented graphically, as plots of average value versus time. For each endpoint in at least ordinal scale, the differences between time periods for each experimental group were tested for nominal significance using non-parametric test (Wilcoxon Signed Rank Test or Sign Test). Differences in the distribution between the experimental arms were tested using non-parametric Chi-square Test. For those numerical endpoints that were found to have normally distributed data, the experimental groups were compared using Independent t-test for group differences at each time point. Additionally, within-group changes from baseline to each subsequent time point were assessed using paired sample t-test. For non-normally distributed numerical endpoints, the experimental groups were compared using Wilcoxon Mann-Whitney test for group differences at each time point. Further, within-group changes from baseline to each subsequent time point were evaluated using Wilcoxon Signed Ranks test or Sign test.

A Modified per Protocol (Mod PP) analysis was performed to assess the efficacy variables of the study. Subjects with at least one completed post-dose visit were included in the analysis. All numeric/continuous efficacy variables were tested for normality and were analyzed by Analysis of Covariance (ANCOVA). In the analysis, the value of the efficacy variable at every time point was modeled as a function of the treatment group (predictor variable of interest) and of the value of that efficacy variable at Baseline (covariate). The analysis would have revealed significant efficacy if the coefficient of the treatment group variable was significantly different from zero and in the right direction. The ANCOVA approach was used to mathematically compensate for the subject's baseline characteristics that happen to be substantially unbalanced between the two treatment groups. This was more efficient than the simpler Student t-test since it adjusts for possible situations like "regression to the mean" and "floor effects".

To obtain comparable documentation on Adverse Events (AEs), the investigator asked the subject a set of open and standardized questions at each visit. The frequency and intensity of AEs and serious AEs were recorded in detail, based on the subject's interviews during each visit. Recorded AEs were grouped by general type of events. Differences in AE patterns between experimental groups were assessed by McNemar Change test.

Example 2 Effects of C16:1n7-Palmitoleate on Joint Function

As shown in FIG. 1, of the 112 subjects screened for this study, 40 subjects were randomly assigned to the C16:1n7-palmitoleate-treated group (n=20) and the placebo group (n=20). A total of 38 subjects were retained through completion of the clinical trial.

Time of Onset of Discomfort

The time of onset of discomfort or pain level refers to the time at which the minimum or maximum discomfort or pain level is reached. The time of onset of minimum discomfort or pain level refers to the time at which minimum discomfort or pain level is reached. The time of onset of maximum discomfort or pain level refers to the time at which maximum discomfort or pain level is reached.

FIG. 2 shows that C16:1n7-palmitoleate treatment increased the time of onset of minimum discomfort or pain level. Within-group analyses revealed that subjects treated with C16:1n7-palmitoleate exhibited a statistically significant increase in the time to reach the minimum pain level at 7 days (p=0.013) and 30 days (p=0.005) compared to that observed at Day 0. These results suggest that subjects were able to exercise a little longer, before the minimum pain level or discomfort was reported. There was no statistically significant difference in the time of onset of minimum discomfort or pain level between the C16:1n7-palmitoleate-treated and placebo groups.

As shown in FIG. 2, the effects of C16:1n7-palmitoleate treatment on the time of onset of maximum discomfort or pain level were evident after 30 days of supplementation. Within-group analyses revealed that the time of onset of maximum discomfort in C16:1n7-palmitoleate-treated subjects was significantly increased after 30 days of treatment compared to that observed at Day 0 (p=0.012). By contrast, the time of onset of maximum discomfort or pain level in the placebo group was decreased after 30 days.

FIG. 2 demonstrates that the time to reach maximum discomfort or pain level was significantly different between the C16:1n7-palmitoleate-treated and placebo groups, with the C16:1n7-palmitoleate-treated subjects taking more time to reach maximum discomfort or pain level. The average time to report maximum discomfort or pain level in the C16:1n7-palmitoleate-treated group after 30 days was 6.89±2.59 minutes compared to the 5.43±2.53 minutes of the placebo group. Changes in the time of onset of maximum discomfort from Day 0 to Day 30 also revealed a statistically significant difference between the C16:1n7-palmitoleate-treated and placebo groups (p=0.007). These results suggest that unlike the placebo group, subjects treated with C16:1n7-palmitoleate were able to exercise a little longer, before the maximum pain level or discomfort was reported.

Time of Offset of Discomfort

As used herein, the time of offset of discomfort is the time at which a level of relief is reached after performing the Stepmill Protocol described herein. The time of offset of minimum discomfort refers to the time at which the subject experiences slight (minimal) relief of discomfort after executing the Stepmill Protocol. The time of offset of maximum discomfort refers to the time at which the subject experiences a minimum level of discomfort (most relief) after executing the Stepmill Protocol.

There was no statistically significant difference in the time of offset of minimum discomfort between the C16:1n7-palmitoleate-treated and placebo groups at any time point. See FIG. 3. Moreover, within-group analyses also showed that there were no statistically significant changes in the time of minimum offset of discomfort from baseline to any time point for both the C16:1n7-palmitoleate-treated and placebo groups.

As shown in FIG. 3, within-group analyses revealed that subjects treated with C16:1n7-palmitoleate for 30 days exhibited a decrease in the time of offset of maximum discomfort (i.e., reduction in the time to reach the minimum level of discomfort after executing the Stepmill Protocol) compared to that observed at Day 0 (p=0.014). There was no statistically significant difference in the time of offset of maximum discomfort between the C16:1n7-palmitoleate-treated and placebo groups at any time point.

6-Minute Timed Walk

There was no statistically significant difference in the distance covered during the 6-minute timed walk between the C16:1n7-palmitoleate-treated and placebo groups at any time point. However, within-group analyses showed that there was a statistically significant change in the distance covered during the 6-minute timed walk in the C16:1n7-palmitoleate-treated group after 30 days of treatment compared to that observed at Day 0 (p=0.036). See FIG. 4.

Knee Extension—Left and Right

Goniometric measurements, which record the active and passive range of motion in joints like the knee, are often used in evaluating joint function.

C16:1n7-palmitoleate treatment resulted in improvements in the range of knee extension. As shown in FIG. 5, subjects treated with the C16:1n7-palmitoleate composition for 30 days had an average increase in left knee extension compared to that observed at Day 0.

According to the within-group analyses shown in FIG. 5, subjects treated with C16:1n7-palmitoleate for 30 days exhibited a significant increase in left knee extension compared to that observed at Day 0 (p=0.028). By contrast, the placebo group exhibited a non-significant decrease in left knee extension at Day 30.

There was no statistically significant difference in right knee extension measurements between the C16:1n7-palmitoleate-treated and placebo groups at any time point. Moreover, within-group analyses also showed that there were no statistically significant changes in right knee extension from baseline to any time point for both the C16:1n7-palmitoleate-treated and placebo groups.

Knee Flexion—Left and Right

C16:1n7-palmitoleate treatment resulted in improvements in the range of knee flexion. As shown in FIG. 6, the effects of C16:1n7-palmitoleate treatment on the change in left knee flexion were apparent after only 7 days of supplementation. By Day 30, C16:1n7-palmitoleate-treated subjects had an average increase in left knee flexion compared to that observed at Day 0. See FIG. 6.

According to the within-group analyses shown in FIG. 6, subjects treated with C16:1n7-palmitoleate for 30 days exhibited a significant increase in left knee flexion compared to that observed at Day 0 (p=0.015). By contrast, no statistically significant changes in left knee flexion were observed in the placebo group between Day 0 and Day 30.

There was no statistically significant difference in right knee flexion measurements between the C16:1n7-palmitoleate-treated and placebo groups at any time point. However, according to the within-group analyses shown in FIG. 6, subjects treated with C16:1n7-palmitoleate for 30 days exhibited a significant increase in right knee flexion compared to that observed at Day 0 (p=0.019). By contrast, the placebo group exhibited a non-significant increase in right knee flexion at Day 30 relative to that observed at Day 0.

Stanford Exercise Scale—Stretching and Aerobics

There were no statistically significant differences in the average minutes per week for aerobic exercise between the C16:1n7-palmitoleate-treated and placebo groups at any time point. See FIG. 7. Within-group analyses showed that there were no statistically significant changes in average minutes per week for aerobic exercise from baseline to any time point for both the C16:1n7-palmitoleate-treated and placebo groups.

There were no statistically significant differences in the average minutes per week for stretching exercise between the C16:1n7-palmitoleate-treated and placebo groups at any time point. However, within-group analyses demonstrated that the C16:1n7-palmitoleate-treated group still exhibited a non-statistically significant yet clinically significant increase in the time spent stretching after 30 days of supplementation (p=0.066). See FIG. 7.

SF-12—Physical and Mental Health Component

There were no statistically significant differences in the physical component score of the SF-12 survey between the C16:1n7-palmitoleate-treated and placebo groups at any time point.

However, according to the within-group analyses shown in FIG. 8, subjects treated with C16:1n7-palmitoleate for 30 days exhibited an 8.93% increase in the physical component score of the SF-12 survey compared to that observed at Day 0 (p=0.031). The placebo group also displayed statistically significant increases of 7.23% and 15.53% in the physical component score of the SF-12 survey at Day 7 (p=0.020) and Day 30 (p=0.008), respectively compared to that observed at Day 0.

There were no statistically significant differences in the mental component score of the SF-12 survey between the C16:1n7-palmitoleate-treated and placebo groups at any time point. Moreover, within-group analyses also showed that there were no statistically significant changes in the mental component score of the SF-12 survey from baseline to any time point for both the C16:1n7-palmitoleate-treated and placebo groups.

Knee-Related Quality of Life Scale

There were no statistically significant differences in knee-related quality of life scores between the C16:1n7-palmitoleate-treated and placebo groups at any time point.

However, according to the within-group analyses shown in FIG. 9, subjects treated with C16:1n7-palmitoleate exhibited an increase in knee-related quality of life scores at Day 7 (p=0.002) and Day 30 (p<0.001), respectively compared to that observed at Day 0. The placebo group also displayed a statistically significant increase in the knee-related quality of life score at Day 30 compared to that observed at Day 0 (p=0.003).

Knee Discomfort Improvement

Figure 10:
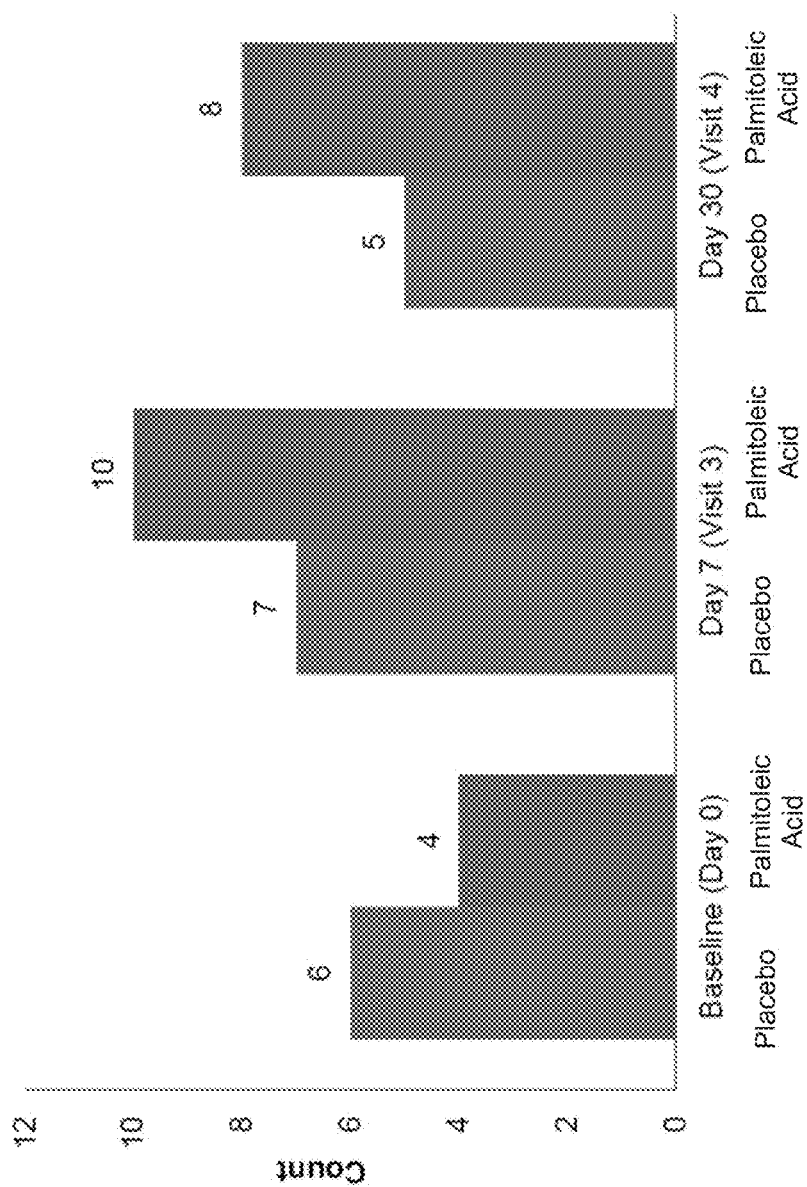
FIG. 10 shows the number of subjects in the C16:1n7-palmitoleate-treated and placebo groups that experienced moderate improvement in knee discomfort.

As shown in FIG. 10, the number of C16:1n7-palmitoleate-treated subjects that reported moderate improvements in knee discomfort increased from 4 at Day 0 to 10 at Day 7. By contrast, only one additional subject from the placebo group reported moderate improvements in knee discomfort at Day 7. Further, 8 subjects within the C16:1n7-palmitoleate-treated group reported moderate improvements in knee discomfort at Day 30. See FIG. 10. Only 5 subjects in the placebo group reported moderate improvements in knee discomfort at Day 30.

Figure 11:
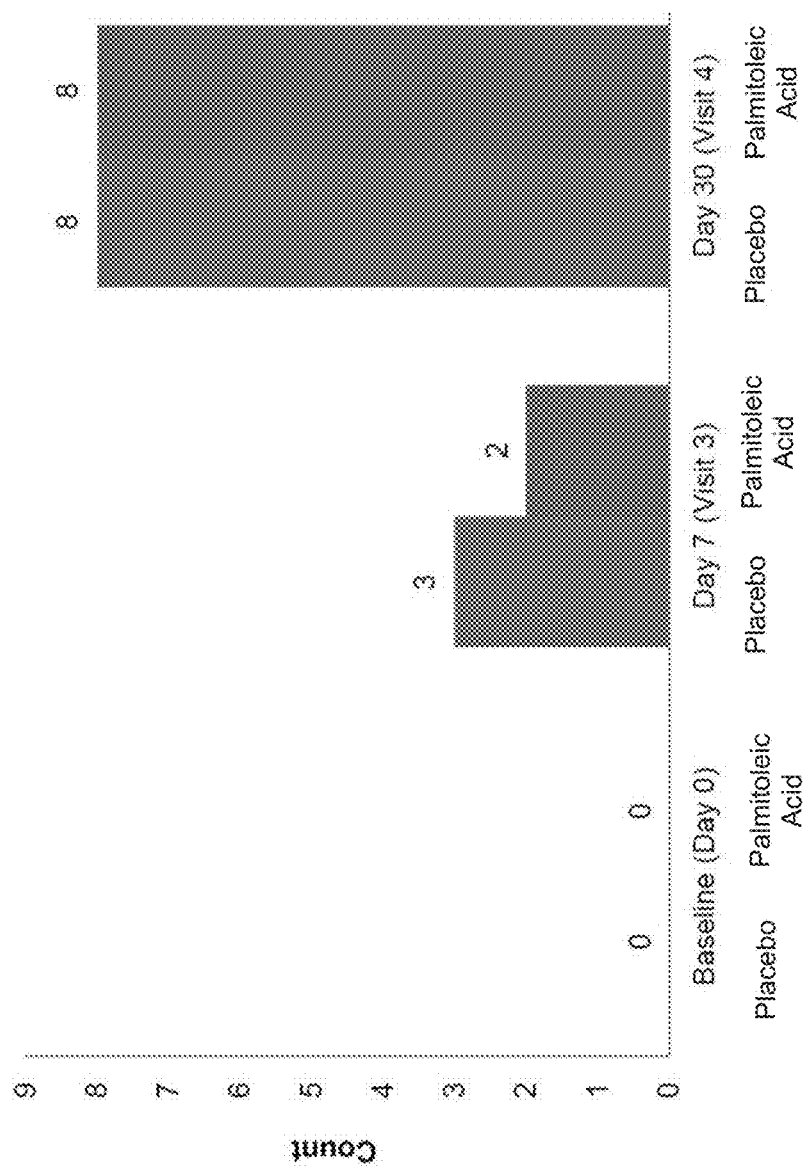
FIG. 11 shows the number of subjects in the C16:1n7-palmitoleate-treated and placebo groups that experienced definite improvement in knee discomfort.

FIG. 11 shows that the number of C16:1n7-palmitoleate-treated subjects that reported definite improvements in knee discomfort increased from 2 at Day 7 to 8 at Day 30, which was comparable to that observed in the placebo group (from 3 subjects at Day 0 to 8 at Day 30). This outcome was not unexpected given that the study was carried out with healthy individuals who did not possess any joint problems at rest. Moreover, these questionnaires and the 6-minute timed walk were designed and clinically validated to measure the severity of arthritis in unhealthy individuals.

These results demonstrate that compositions comprising C16:1n7-palmitoleate are useful in improving joint function in individuals undergoing physical exercise. Specifically, subjects treated with C16:1n7-palmitoleate exhibit an increase in the time of onset of maximum discomfort, and increased range of motion in the knee joint. As such, C16:1n7-palmitoleate, derivatives thereof, pharmaceutically acceptable salts thereof, or a combination thereof, are useful in methods for improving joint function in human subjects.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for improving joint function in a subject in need thereof comprising administering to the subject an effective amount of a composition comprising a C16:1n7-palmitoleate derivative in an amount of at least about 20 wt % and a C16:0-palmitate derivative, thereby improving joint function, wherein joint function is improved in the subject when a delay in time of onset of maximum joint discomfort or pain at a level of 5 or greater on an eleven-point LIKERT scale is detected in the subject compared to the time of onset of maximum joint discomfort or pain at a level of 5 or greater on the eleven-point LIKERT scale observed in the subject prior to administration of the composition, wherein the C16:1n7-palmitoleate derivative is palmitoleic acid, a pharmaceutically acceptable salt of palmitoleate, a $(C_1-C_8)$ alkyl ester of palmitoleate, a monoglyceride of palmitoleic acid, a diglyceride of palmitoleic acid, or a triglyceride of palmitoleic acid; and wherein the C16:0-palmitate derivative is palmitic acid, a pharmaceutically acceptable salt of palmitate, a $(C_1-C_8)$alkyl ester of palmitate, a monoglyceride of palmitic acid, a diglyceride of palmitic acid, or a triglyceride of palmitic acid.

2. The method of claim 1, wherein the composition further comprises a C18:1n9-oleate derivative wherein the C18:1n9-oleate derivative is oleic acid, a pharmaceutically acceptable salt of oleate, a $(C_1-C_8)$alkyl ester of oleate, a monoglyceride of oleic acid, a diglyceride of oleic acid, or a triglyceride of oleic acid.

3. The method of claim 1, wherein the composition comprises at least about 30 wt % of the C16:1n7-palmitoleate derivative.

4. The method of claim 1, wherein the subject experiences joint pain while engaging in moderate, hard, or very hard physical activity.

5. The method of claim 1, wherein the subject is human.

6. The method of claim 1, further comprising simultaneously, sequentially, or separately administering at least one additional therapeutic agent.

7. The method of claim 1, wherein the composition is administered orally, topically, systemically, intravenously, subcutaneously, intraperitoneally, or intramuscularly.

8. The method of claim 1, wherein the composition is administered daily for 4 weeks or more.

9. The method of claim 1, wherein administration of the composition causes the delay in the time of onset of maximum joint discomfort or pain in the subject.

10. The method of claim 9, wherein the time of onset of maximum discomfort or pain level in the subject is delayed by at least 20%.

11. The method of claim 6, wherein the at least one additional therapeutic agent is selected from the group consisting of acetaminophen, ibuprofen, naproxen sodium, Cox-2 inhibitors, muscle relaxants, opioids, antidepressants, antiepileptic drugs, topical agents, methyl salicylate, capsaicin, steroid injections, and hyaluronan injections.

12. The method of claim 1, wherein administration of the composition causes an increase in the range of joint motion in the subject.

13. The method of claim 12, wherein the range of joint motion is increased by at least 10%.

14. The method of claim 1, wherein the composition is obtained from fish.

15. The method of claim 1, wherein administration of the composition after 30 days results in an improvement in joint function in the subject relative to the joint function observed in the subject prior to administration.

16. The method of claim 2, further comprising simultaneously, sequentially, or separately administering at least one additional therapeutic agent.

17. The method of claim 3, further comprising simultaneously, sequentially, or separately administering at least one additional therapeutic agent.

* * * * *